US00PP30117P2

(12) United States Plant Patent
Trees

(10) Patent No.: US PP30,117 P2
(45) Date of Patent: Jan. 15, 2019

(54) ***HELIANTHUS* PLANT NAMED 'AUTUMN GOLD'**

(50) Latin Name: *Helianthus salicifolius*
Varietal Denomination: Autumn Gold

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/732,237

(22) Filed: Oct. 10, 2017

(51) Int. Cl.
*A01H 5/02* (2018.01)

(52) U.S. Cl.
USPC ..... Plt./436

(58) Field of Classification Search
USPC ..... Plt./263.1, 436
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Helianthus* plant named 'Autumn Gold', characterized by its single-type, golden-yellow colored inflorescences, dark green-colored foliage, moderately vigorous, and compact-mounded growth habit, is disclosed.

1 Drawing Sheet

Latin name of genus and species of plant claimed: *Helianthus salicifolius.*

Variety denomination: 'Autumn Gold'.

BACKGROUND OF THE INVENTION

The present invention relates to a new and distinct cultivar of *Helianthus* plant botanically known as *Helianthus salicifolius* and hereinafter referred to by the cultivar name 'Autumn Gold'.

The new cultivar originated in a controlled breeding program in Guadalupe, Calif. during September 2009. The objective of the breeding program was the development of *Helianthus* cultivars that are early to flower and have compact habits.

The new *Helianthus* cultivar was the result of a self-pollination of 'Low Down', U.S. Plant Pat. No. 13,197, characterized by its single-type, bright yellow-colored inflorescences, medium green-colored foliage, and moderately vigorous, compact-mounded growth habit. The new cultivar was discovered and selected as a single flowering plant within the progeny of the above stated self-pollination during October 2010 in a controlled environment in Guadalupe, Calif.

Asexual reproduction of the new cultivar by terminal stem cuttings since October 2010 in Guadalupe, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Autumn Gold' as a new and distinct cultivar of *Helianthus* plant:

1. Single-type, golden-yellow colored inflorescences;
2. Dark green-colored foliage;
3. Moderately vigorous, and compact-mounded growth habit.

Plants of the new cultivar differ from plants of the parent primarily in having smaller diameter inflorescences.

Of the many commercially available *Helianthus* cultivars, the most similar in comparison to the new cultivar is 'First Light', U.S. Plant Pat. No. 13,150. However, in side-by-side comparisons, plants of the new cultivar differ from plants of 'First Light' in at least the following characteristics:

1. Plants of the new cultivar have a shorter and more mounded growth habit than plants of 'First Light';
2. Plants of the new cultivar flowered 7 to 10 days earlier than plants of 'First Light'; and
3. Plants of the new cultivar have smaller diameter inflorescences than plants of 'First Light'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Autumn Gold'. The plants were approximately 8-months old. They were grown in one-gallon containers in a greenhouse for approximately 2 months and then transplanted into an outdoor garden bed in West Chicago, Ill. and grown for an additional 6 months. Plants were given two pinches prior to transplant into the containers.

DETAILED BOTANICAL DESCRIPTION

Figure 1:
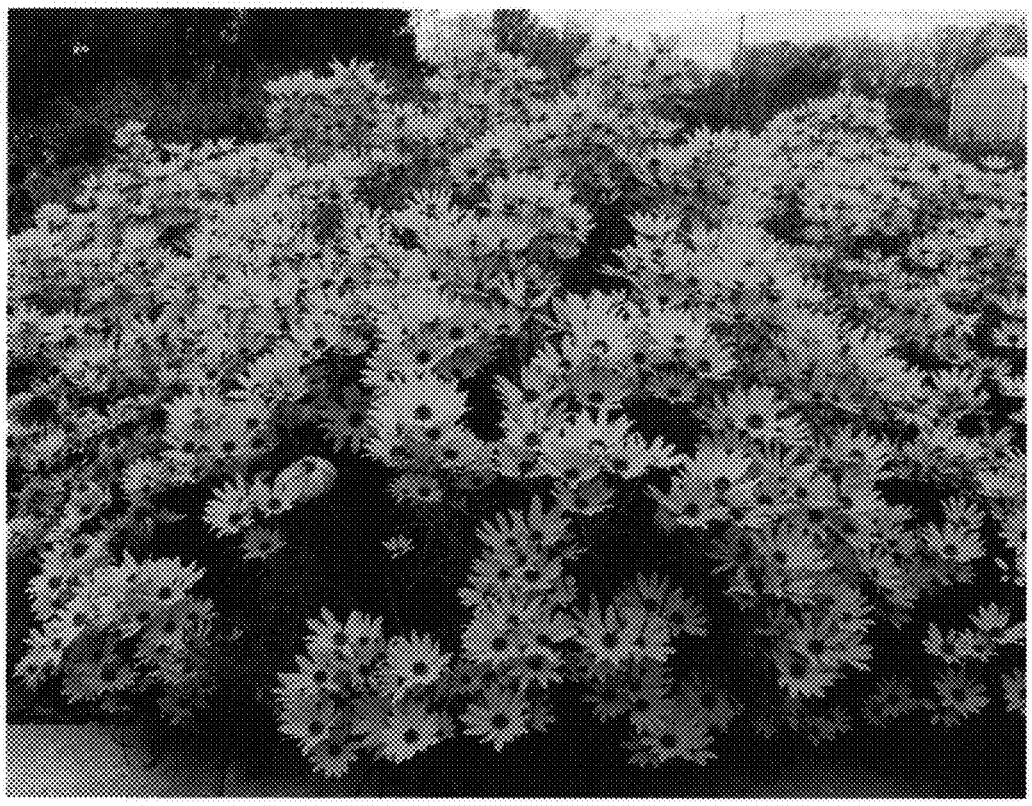
FIG. 1 illustrates a side view of the overall growth and flowering habit of 'Autumn Gold'.
Figure 2:
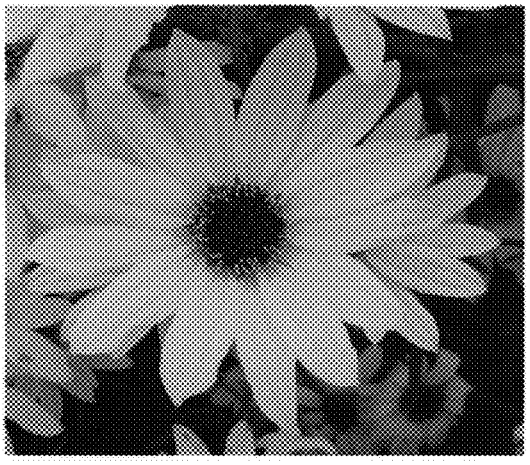
FIG. 2 illustrates a close-up view of an individual inflorescence of 'Autumn Gold'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in September 2017 under natural light conditions in West Chicago, Ill.

The following descriptions and measurements describe 8-month old plants produced from cuttings from stock plants and grown under conditions comparable to those used in commercial practice. The plants were grown in one-gallon containers for approximately 2 months in a greenhouse and then transplanted into an outdoor garden bed in West Chicago, Ill. and grown for an additional 6 months. Plants were given two pinches prior to transplant into the containers. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Helianthus salicifolius* 'Autumn Gold'.

Parentage:

*Female and male parent.*—'Low Down', U.S. Plant Pat. No. 13,197.

Propagation:

*Type cutting.*—Terminal stem.

*Time to initiate roots.*—Approximately 10 to 12 days.

*Time to produce a rooted cutting.*—Approximately 35 to 42 days.

*Root description.*—Fibrous, fine, generally white to light brown in color.

*Rooting habit.*—Freely branching.

Plant description:

*Commercial crop time.*—Approximately 12 to 14 weeks from a rooted cutting to finish in a 15 cm pot.

*Growth habit and general appearance.*—Perennial, moderately vigorous, compact-mounded.

*Hardiness.*—USDA Zone 5a (−20° F. to −15° F./−28.9 ° C. to −26° C.).

*Size.*—Height from soil level to top of plant plane: Approximately 73.0 cm. Width: Approximately 85.0 cm.

*Branching habit.*—Freely branching, pinching enhances basal branching. Quantity of main branches per plant: Approximately 3 with each having approximately 10 lateral branches.

*Lateral branch.*—Strength: Strong, laterals somewhat brittle. Length to base of inflorescence: Approximately 40.0 cm. Diameter: Approximately 5.0 mm. Length of central internode: Approximately 9.0 mm. Texture: Moderately pubescent with short stiff hairs. Color of young stem: 146C. Color of mature stem: 146C, becoming woody 200A with age.

Foliage description:

*General description.*—Quantity of leaves per lateral branch: Approximately 40. Fragrance: None detected. Form: Simple. Arrangement: Primarily alternate, opposite at branch base.

*Leaves.*—Aspect: Arched downward. Shape: Linear. Margin: Entire, leaf margins curve downwards enclosing the lower surface of the leaf Apex: Acute. Base: Sessile. Venation pattern: Pinnate, only midvein visible. Length of mature leaf: Approximately 8.2 cm. Width of mature leaf: 4.0 mm. Texture of upper surface: Sparsely pubescent with short stiff hairs. Texture of lower surface: Tomentose. Color of upper surface of young foliage: Closest to 137A with colorless midvein, other venation indistinguishable. Color of lower surface of young foliage: Closest to 137B but appears NN155D due to pubescence; with colorless midvein, other venation indistinguishable. Color of upper surface of mature foliage: Closest to NN137A with colorless midvein, other venation indistinguishable. Color of lower surface of mature foliage: Closest to NN137B, but appears NN155D due to pubescence; colorless midvein, other venation indistinguishable.

Flowering description:

*Flowering habit.*—'Autumn Gold' is freely flowering under outdoor growing conditions with substantially continuous blooming from September through November.

*Lastingness of individual inflorescence on the plant.*—Approximately 4 weeks.

Inflorescence description:

*General description.*—Type: Single-type, in open, panicle-like clusters. Persistent. Shape: Round. Aspect: Upward and outward facing. Arrangement: Terminal capitulum, positioned above the foliage. Quantity per plant: Approximately 300. Diameter: Approximately 5.5 cm. Depth: Approximately 2.5 cm. Fragrance: None detected.

*Peduncle.*—Strength: Strong, somewhat flexible. Aspect: Erect. Length: Approximately 3.0 cm to 4.0 cm. Diameter: Approximately 2.0 mm. Texture: Densely pubescent. Color: 146C.

*Bud.*—Rate of opening: Generally takes 5 to 7 days for bud to progress from first color to fully open flower.

*Bud just before opening.*—Shape: Flattened globular. Diameter: Approximately 7.0 mm. Color: 144D.

*Ray florets.*—Quantity per inflorescence: Approximately 13 to 19. Appearance: Dull. Arrangement: Imbricate, in one or two whorls. Aspect: Acute angle to disc. Shape: Oblong. Margin: Entire. Apex: Emarginate. Base: Attenuate. Length: Approximately 2.8 cm. Width: Approximately 9.0 mm. Texture of upper and lower surfaces: Glabrous, ribbed longitudinally. Color of upper surface when first open: 14A. Color of lower surface when first open: 14B. Color of upper surface when fully open: 15A to 15B. Color of lower surface when fully open: 15B to 15C.

*Disc florets.*—Quantity per inflorescence: Approximately 125. Arrangement: Massed in center of inflorescence Shape: Tubular. Margin: Entire. Apex: Five acute tips. Base: Fused. Length: Approximately 7.0 mm. Diameter at apex: Approximately 1.5 mm. Diameter at base: Approximately 1.0 mm. Texture: Glabrous with sparsely pubescent centers. Color when fully open: tips of closest to but more brown than 187A, centers of 3D and NN155A at base.

*Disc.*—Diameter: Approximately 1.1 cm. Depth: Approximately 1.0 cm.

*Receptacle.*—Shape: Dome. Height: Approximately 2.0 mm. Diameter at base: Approximately 5.0 mm. Color: 155C.

*Phyllaries*.—Quantity per inflorescence Approximately 43. Arrangement: In two to three whorls. Shape: Narrowly lanceolate. Margin: Entire. Apex: Acute. Base: Truncate. Length: Approximately 7.0 mm to 1.0 cm. Width: Approximately 2.0 mm at base. Texture of upper surface: Glabrous. Texture of lower surface: Densely pubescent. Color of upper and lower surfaces: 137A with base of 138B.

*Reproductive organs*.—Androecium: Present on disc florets only. Stamen quantity: 5. Stamen length: Approximately 3.0 mm. Anther shape: Linear. Anther length: Approximately 2.5 mm. Anther color: Closest to 203B. Filament color: 155D. Pollen amount: Abundant. Pollen color: 14A. Gynoecium: Present on ray and disc florets. Pistil quantity: 1 per floret. Pistil length: Approximately 7.0 mm. Stigma shape: Bifid. Stigma length: Approximately 1.0 mm. Stigma color: 14B. Style length: Approximately 4.0 mm. Style color: 150D. Ovary length: Approximately 2.0 mm. Ovary color: NN155A.

Seed and fruit production: Neither seed nor fruit production has been observed.

Disease and pest resistance: Resistance to pathogens and pests common to *Helianthus* has not been observed.

What is claimed is:

1. A new and distinct cultivar of *Helianthus* plant named 'Autumn Gold', substantially as herein illustrated and described.

* * * * *